United States Patent
Perbost (12)

(10) Patent No.: US 6,451,998 B1
(45) Date of Patent: Sep. 17, 2002

(54) CAPPING AND DE-CAPPING DURING OLIGONUCLEOTIDE SYNTHESIS

(75) Inventor: Michael G. M. Perbost, Cupertino, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/420,099

(22) Filed: Oct. 18, 1999

(51) Int. Cl.[7] ............................................. C07H 21/00
(52) U.S. Cl. ........................ 536/25.31; 536/25.33; 536/25.34
(58) Field of Search .................. 530/25.31, 25.33, 530/25.34

(56) References Cited

U.S. PATENT DOCUMENTS

| | | | |
|---|---|---|---|
| 4,415,732 A | 11/1983 | Caruthers et al. | 536/25.34 |
| 4,458,066 A | 7/1984 | Caruthers et al. | 536/25.34 |
| 4,500,707 A | 2/1985 | Caruthers et al. | 536/25.34 |
| 4,816,571 A | 3/1989 | Andrus et al. | 536/25.34 |
| 5,049,656 A * | 9/1991 | Lewis et al. | 530/334 |
| 5,153,319 A | 10/1992 | Caruthers et al. | 536/25.34 |
| 5,218,103 A | 6/1993 | Caruthers et al. | 536/25.33 |
| 5,221,736 A * | 6/1993 | Coolidge et al. | 536/25.31 |
| 5,393,877 A | 2/1995 | McLean et al. | 536/25.34 |
| 5,464,759 A * | 11/1995 | Coolidge et al. | 435/91.2 |
| 5,552,535 A | 9/1996 | McLean et al. | 536/23.1 |
| 5,681,945 A | 10/1997 | McLean et al. | 536/25.34 |
| 5,824,793 A | 10/1998 | Hirschbein et al. | 536/25.34 |
| 5,856,464 A | 1/1999 | Livingston | 536/25.3 |
| 5,861,256 A | 1/1999 | Glass et al. | 435/6 |
| 5,869,643 A | 2/1999 | Chatelain et al. | 536/25.3 |
| 5,886,193 A | 3/1999 | McLean et al. | 548/544 |
| 5,908,926 A | 6/1999 | Pirrung et al. | 536/25.34 |

FOREIGN PATENT DOCUMENTS

| | | |
|---|---|---|
| EP | 0294196 B1 | 3/1996 |
| WO | WO 86/07362 A1 | 12/1986 |
| WO | WO 93/20091 A1 | 10/1993 |
| WO | WO 93/20092 A1 | 10/1993 |

OTHER PUBLICATIONS

Sekine et al., "Chemical Synthesis of a 5'-Terminal TMG-Capped Triribonucleotide $m_3^{2,2,7}G^{5'}$ pppAmpUmpA of U1 RNA," *Journal of Organic Chemistry*, 61(13), 4412–4422 (Jun. 28, 1996).*

Baker et al., "Decapitation of 5'- Capped RNA by an Antisense Copper Complex Conjugate," *Bioorganic & Medicinal Chemistry Letters*, 6(14), 1647–1652 (Jul. 23, 1996).*

Schwartz, M.E. et al., "A Universal Adapter for Chemical Synthesis of DNA or RNA on any Single Type of Solid Support", *Tetrahedron Letters*, vol. 36, No. 1, pp. 27–30, 1995.

(List continued on next page.)

Primary Examiner—Johann Richter
Assistant Examiner—L. Eric Crane
(74) Attorney, Agent, or Firm—Gordon M. Stewart

(57) ABSTRACT

A method of capping a hydroxy group of a moiety, comprising coupling the moiety to a phosphor or phosphite derivative of a protected alcohol, so as to form the corresponding phosphate or phosphite between the hydroxy and phosphor or phosphite groups. The hydroxy group may be later de-capped by hydrolyzing the resulting compound to deprotect the protected alcohol and cleave the phosphate from the moiety so as to regenerate the hydroxy group of the moiety. The method has particular application to fabrication of addressable polynucleotide arrays and allows failed sequences, as well as inter-feature regions, to be left with a free hydroxy group at the ends of the molecules (failed sequences or linkers) at such locations.

24 Claims, 4 Drawing Sheets

R6: $CH_3$, $CH_2$-$CH_2$-CN
R7: isopropyl, any bulky alkyl group
R8: unreacted nucleotide, nucleoside or hydroxyl on the surface of the array

OTHER PUBLICATIONS

Yu, Dong et al., "Diethoxy N,N–diisopropyl Phosphoramidite as an Improved Capping Reagent in the Synthesis of Oligonucleotides Using Phosphoramidite Chemistry", *Tetrahedron Letters*, vol. 35, No. 46, pp. 8565–8568, 1994.

Gough, G.R. et al., "2' (3')–0–Benzoyluridine 5' Linked to Glass: An All–Purpose Support for Solid Phase Synthesis of Oligodeoxyribonucleotides", *Tetrahedron Letters*, vol. 24, No. 48, pp. 5321–5324, 1983.

Uchimaru, T. et al., "RNA Hydrolysis via an Oxyphosphorane Intermediate", *Biochem. & Biophys. Res. Comm.*, vol. 187, No. 3, pp. 1523–1528, Sep. 30, 1992.

deBear, J.S. et al, "A Universal Glass Support for Oligonucleotide Synthesis", *Nucleosides & Nucleotides*, vol. 6, No. 5, pp. 821–830, 1987.

* cited by examiner

R6: $CH_3$, $CH_2\text{-}CH_2\text{-}CN$
R7: isopropyl, any bulky alkyl group
R8: unreacted nucleotide, nucleoside or hydroxyl on the surface of the array

CAPPING AND DE-CAPPING DURING OLIGONUCLEOTIDE SYNTHESIS

FIELD OF THE INVENTION

This invention relates to arrays, particularly polynucleotide arrays such as DNA arrays, which are useful in diagnostic, screening, gene expression analysis, and other applications.

BACKGROUND OF THE INVENTION

Polynucleotide arrays (such as DNA or RNA arrays), are known and are used, for example, as diagnostic or screening tools. Such arrays include regions of usually different sequence polynucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon interrogating the array. For example all polynucleotide targets (for example, DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated by depositing previously obtained biopolymers onto a substrate, or by in situ synthesis methods. The in situ fabrication methods include those described in WO 98/41531 and the references cited therein. The in situ method for fabricating a polynucleotide array typically follows, at each of the multiple different addresses at which features are to be formed, the same conventional iterative sequence used in forming polynucleotides on a support by means of known chemistry. Typically these methods use a nucleoside reagent of the formula:

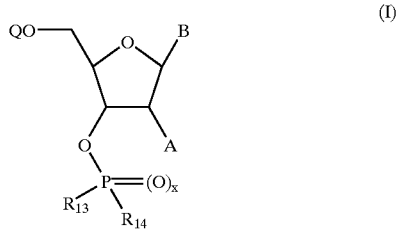

(I)

in which:
  A represents H or an optionally protected hydroxyl group;
  B is a purine or pyrimidine base whose exocyclic amine functional group is optionally protected;
  Q is a conventional protective group for the 5'—OH functional group;
  x=0 or 1 provided:
    a) when x=1:
    $R_{13}$ represents H and $R_{14}$ represents a negatively charged oxygen atom; or
    $R_{13}$ is an oxygen atom and $R_{14}$ represents either an oxygen atom or an oxygen atom carrying a protecting group; and
    b) when x=0, $R_{13}$ is an oxygen atom carrying a protecting group and $R_{14}$ is either a hydrogen or a di-substituted amine group.

When x is equal to 1, $R_{13}$ is an oxygen atom and $R_{14}$ is an oxygen atom, the method is in this case the so-called phosphodiester method; when $R_{14}$ is an oxygen atom carrying a protecting group, the method is in this case the so-called phosphotriester method.

When x is equal to 1, $R_{13}$ is a hydrogen atom and $R_{14}$ is a negatively charged oxygen atom, the method is known as the H-phosphonate method.

When x is equal to 0, $R_{13}$ is an oxygen atom carrying a protecting group and $R_{14}$ is either a halogen, the method is known as the phosphite method and, when $R_{14}$ is a leaving group of the disubstituted amine type, the method is known as the phosphoramidite method.

The conventional sequence used to prepare an oligonucleotide using reagents of the type of formula (I), basically follows the following steps: (a) coupling a selected nucleoside through a phosphite linkage to a functionalized support in the first iteration, or a nucleoside bound to the substrate (i.e. the nucleoside-modified substrate) in subsequent iterations; (b) optionally, but preferably, blocking unreacted hydroxyl groups on the substrate bound nucleoside; (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in a known manner.

The foregoing methods of preparing polynucleotides are described in detail, for example, in Caruthers, *Science* 230: 281–285, 1985; Itakura et al., *Ann. Rev. Biochem.* 53: 323–356; Hunkapillar et al., *Nature* 310: 105–110, 1984; and in "Synthesis of Oligonucleotide Derivatives in Design and Targeted Reaction of Oligonucleotide Derivatives, CRC Press, Boca Raton, Fla., pages 100 et seq., U.S. Pat. No. 4,458,066, U.S. Pat. No. 4,500,707, U.S. Pat. No. 5,153,319, U.S. Pat. No. 5,869,643, EP 0294196, and elsewhere. The phosphoramidite and phosphite triester approaches are most broadly used, but other approaches include the phosphodiester approach, the phosphotriester approach and the H-phosphonate approach.

In the case of array fabrication, different monomers may be deposited at different addresses on the substrate during any one iteration so that the different features of the completed array will have different desired biopolymer sequences. One or more intermediate further steps may be required in each iteration, such as the conventional oxidation and washing steps.

While each iteration of the foregoing sequence can have a very high yield (over 90%), there is still a small portion of the substrate bound moiety with unreacted linking groups (referenced together herein as "failed sequences"). It is known to cap such failed sequences to avoid the growth of undesired polynucleotide sequences from them. Capping compounds are described in the above mentioned references. A conventional capping compound is acetic anhydride which forms an acetate in conjunction with the hydroxy group of the substrate bound moiety. However, the yield of the capping reaction using acetic anhydride is relatively low. U.S. Pat. No. 4,816,571 suggests using a phosphite monoester capping reagent to form, along with the free hydroxy of the failed sequence, a phosphite triester blocking group. However, the present invention recognizes that in the fabrication of addressable arrays, use of such a capping reagent can leave some portions of the surface not carrying the desired polynucleotide sequences, with a different terminal group (a phosphite triester) than other portions since removal of the phosphite (de-capping) is relatively inefficient. This is particularly the case where an array is formed by a method which leaves spaces between the individual features ("interfeature spaces"), such as deposition of droplets of reagents at the desired feature locations, and when capping is performed by exposing an entire functionalized substrate (such as by flooding) with the capping reagent. In such cases, some portions of the functionalized surface may be capped but not others. Due to such differences in interfeature surface composition (specifically, the functional groups left at the end the failed sequences or functionalizing group), background absorption of polynucleotides in a sample being tested onto interfeature areas may vary across the substrate, making identification of a features to which polynucleotides have bound, more difficult. This may be particularly the case where automated systems are used to detect such features, based on patterns observed on the array following exposure to a sample.

It is also known in the context of RNA hydrolysis generally, and in the context of preparing a "universal" solid support upon which oligonucleotides can be synthesized, that a β-phosphotriester group (in relation to a an ester group) of a molecule used to link the growing oligonucleotide to a support, can be hydrolyzed so as to cleave the linker from the support and the phosphate from the linker to provide a 3' hydroxy on the growing oligonucleotide. Such a scheme is disclosed in U.S. Pat. No. 5,681,945 and is illustrated in FIG. 1. Similarly, deBear et al. in *Nucleosides & Nucleotides*, 6(5), 821–830 (1987) also discloses preparation of a universal solid support involving the sequence illustrated in FIG. 2. Additionally, the reaction energy profile involved in reactions of the foregoing type, has been disclosed by Uchimaru et al., *Biochemical and Biophysical Research Communications*, Vol. 187, No. 3, 1523–1528 (1992). The foregoing references, and all other references cited in the present application, are incorporated herein by reference.

It would be desirable then, to provide an alternative method of capping failed sequences in polynucleotide formation. It would further be desirable to provide such a method which can be used in the fabrication of polynucleotide arrays and can provide failed sequences and interfeature areas with a functional group of the same type as provided by the functionalized surface.

SUMMARY OF THE INVENTION

The present invention then, provides a method of capping a hydroxy group of a moiety, comprising coupling the moiety to a β-phosphor or β-phosphite (such as a β-phosphoramidyl), protected alcohol, so as to form the corresponding phosphate or phosphite between the hydroxy and phosphor or phosphite groups.

The invention may include the step of oxidizing any phosphorous ester linkage formed other than a phosphate (for example, phosphite) to the corresponding phosphate. The resulting compound (containing the phosphate group) may then be hydrolyzed to deprotect the protected alcohol and cleave the phosphate from the moiety so as to regenerate the hydroxy group of the moiety.

In another aspect, the present invention provides a method of capping and de-capping a hydroxy group of a moiety. In this aspect, the hydroxy group may be capped as described above, and de-capped by hydrolyzing the resulting compound to deprotect the protected alcohol and cleave the phosphate from the moiety so as to regenerate the hydroxy group of the moiety. The de-capping may be performed under suitable conditions, such as those described in deBear et al., cited above. For example, the hydrolysis may be performed under alkaline conditions.

In one aspect, the above method is applied to a method of synthesizing oligonucleotides on a substrate carrying substrate bound moieties each with a hydroxy group (such as a functionalized substrate surface or a hydroxy group of a substrate bound nucleotide). In this aspect, in a coupling step a first nucleoside carrying a phosphor or phosphite group is coupled to the hydroxy group of at least some of the substrate bound moieties in the usual manner. The first nucleoside has a protected hydroxy which can be deprotected under first deprotection conditions. In the case of phosphoramidite chemistry, this coupling step results in forming the corresponding phosphite between the hydroxy groups of the substrate bound moieties and the phosphoramidyl groups of the first phosphoramidite. At least some of the substrate bound moieties which failed to couple with the nucleoside phosphoramidite are capped in a capping step, by exposing them to a β- or γ-phosphoramidyl, protected alcohol, in the manner described above, which protected alcohol can be deprotected under second deprotection conditions but not the first deprotection conditions. In the case of phosphoramidite chemistry, this forms the corresponding phosphite between the hydroxy of those substrate bound moieties, and phosphoramidyl group of the β- or γ-phosphoramidyl, protected alcohol.

The oligonucleotide synthesis method of the present invention may include, following the foregoing capping, a deprotection step in which the substrate is exposed to the first deprotection conditions to deprotect the protected hydroxy of the coupled nucleoside in a manner already described. The sequence of the coupling, capping, de-capping steps, and de-protecting, may be repeated as often as required to form a desired polynucleotide, with the deprotected hydroxy of the coupled nucleoside from the deprotection step in one cycle of the steps, serving as the hydroxy group of substrate bound moieties in the next cycle. When all desired cycles are complete, the substrate may be exposed to the second deprotection conditions to de-cap failed sequences by hydrolysis in the manner already described, so as to regenerate the hydroxy group of the substrate bound moiety. It will be understood, of course, that there may be other optional steps provided in each cycle or at the end of all desired cycles. For example, an oxidation step may be provided to oxidize internucleoside phosphites to the more stable corresponding phosphates, and one or more washing steps may also be provided.

The present invention further includes, in another aspect, a method of fabricating an addressable array of polynucleotides on a substrate carrying substrate bound moieties each with a hydroxy group. This method includes, at each of multiple different substrate addresses, executing the above described oligonucleotide synthesis method of the present invention (particularly, including the described capping and de-capping steps). The phosphoramidites to be coupled at respective addresses may, for example, be deposited as droplets at those addresses, and wherein in the capping step at least inter-address areas (and preferably both address and inter-address areas) are exposed to the β- or γ-phosphor or phosphite (for example, phosphoramidyl), protected alcohol.

The various aspects of the present invention can provide any one or more of a number of useful benefits. For example, an alternative method of capping failed sequences in polynucleotide formation is provided which does not require use of acetic anhydride. The method can be used in the fabrication of polynucleotide arrays and can provide failed sequences and interfeature areas with a functional group of the same type as provided by the functionalized surface.

BRIEF DESCRIPTION OF THE DRAWINGS

To facilitate understanding, identical reference numerals have been used, where practical, to designate identical elements that are common to the figures.

DETAILED DESCRIPTION OF EMBODIMENTS OF THE INVENTION

Figure 1:
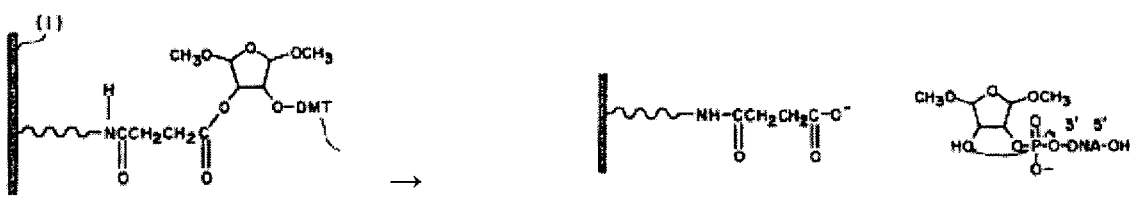
FIGS. 1 and 2 illustrate known schemes in the use of universal supports for polynucleotide synthesis, as discussed in the "Background" section above.
Figure 2:
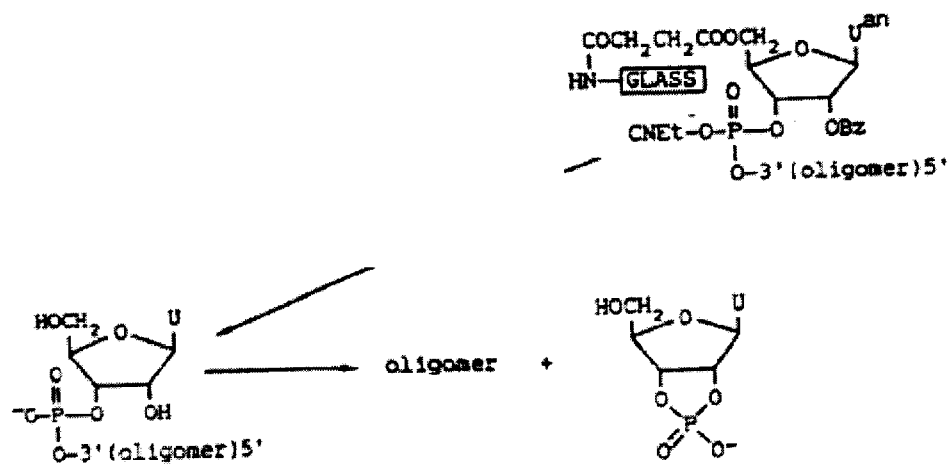

Throughout the present application, unless a contrary intention appears, the following terms refer to the indicated characteristics. A "biopolymer" is a polymer of one or more types of repeating units. Biopolymers are a type of polymer found in biological systems and particularly include peptides or polynucleotides, as well as such compounds composed of or containing amino acid or nucleotide analogs or non-nucleotide groups. This includes polynucleotides in which the conventional backbone has been replaced with a non-naturally occurring or synthetic backbone, and nucleic acids in which one or more of the conventional bases has been replaced with a synthetic base capable of participating in Watson-Crick type hydrogen bonding interactions. Polynucleotides include single or multiple stranded configurations, where one or more of the strands may or may not be completely aligned with another. While probes and targets of the present invention will typically be single-stranded, this is not essential. A "nucleotide" refers to a sub-unit of a nucleic acid and has a phosphate group, a 5 carbon sugar and a nitrogen containing base, as well as analogs of such sub-units. Specifically, a "biopolymer" includes DNA (including cDNA), RNA and oligonucleotides, regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have a removable protecting groups). A biomonomer fluid or biopolymer fluid reference a liquid containing either a biomonomer or biopolymer, respectively (typically in solution). An "array", unless a contrary intention appears, includes any one or two dimensional arrangement of addressable regions bearing a particular chemical moiety to moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers to one or more characteristics of the array, such as feature positioning, feature size, and some indication of a moiety at a given location. "Hybridizing" and "binding", with respect to polynucleotides, are used interchangeably. A "phosphor" group includes a phosphodiester, phosphotriester, and H-phosphonate groups as defined in connection with formula (1) above, while a "phosphite" includes a phosphoramidite (in the case of either a phosphor or phosphite group, a moiety other than the illustrated substituted 5-membered furyl ring may be attached to O of the phosphor or phosphite group which links between the furyl ring shown in formula (I) and the P atom). A "lower" alkyl, carboxylate or other "lower" group, references such a group having from 1 to 6 carbon atoms. A "protecting group" is used in the conventional chemical sense to reference a group which reversibly renders unreactive a functional group under specified conditions of a desired reaction. After the desired reaction, protecting groups may be removed to deprotect the protected functional group. To avoid confusion, the —OH group of a nucleoside monomer (typically, the 3' or 5' —OH of a nucleoside phosphoramidite) which is protected then deprotected during each cycle of polynucleotide coupling, is generally referenced as a "hydroxy", while —OH of the nucleoside monomer which is generally only deprotected after the desired polynucleotide synthesis is complete, is referenced as an "alcohol" group (which is typically protected until after such completion). All protecting groups should be removable (and hence, labile) under conditions which do not degrade a substantial proportion of the polynucleotides being synthesized. It is also possible in the present invention that steps may be executed in different sequence where this is logically possible. However, the sequence described below is preferred.

It will also be appreciated that throughout the present application, that words such as "upper", "lower" are used in a relative sense only. A "set" may have one type of member or multiple different types. "Fluid" is used herein to reference a liquid. Reference to a singular item, includes the possibility that there are plural of the same items present.

Figure 3:
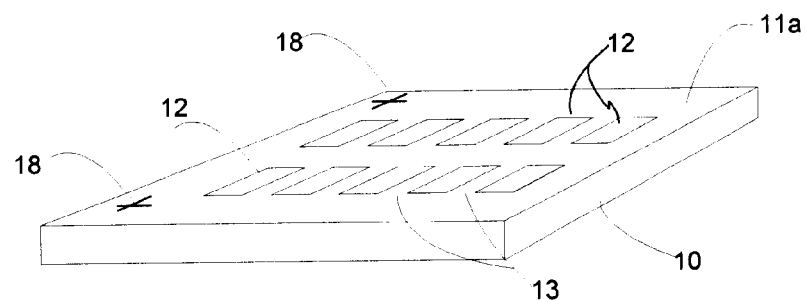
FIG. 3 illustrates a substrate carrying multiple arrays, such as may be fabricated by methods of the present invention.
Figure 4:
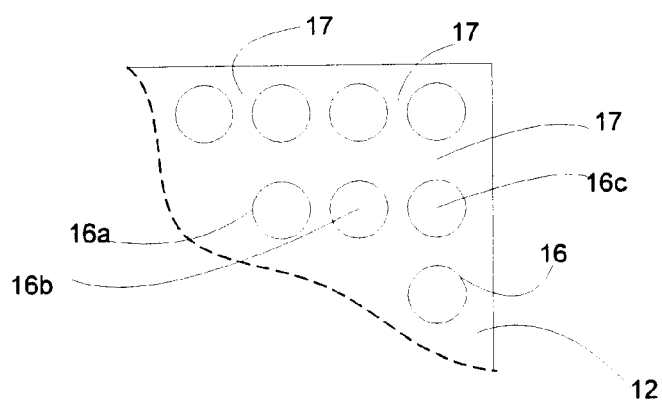
FIG. 4 is an enlarged view of a portion of FIG. 3 showing multiple spots or features of one array.
Figure 5:
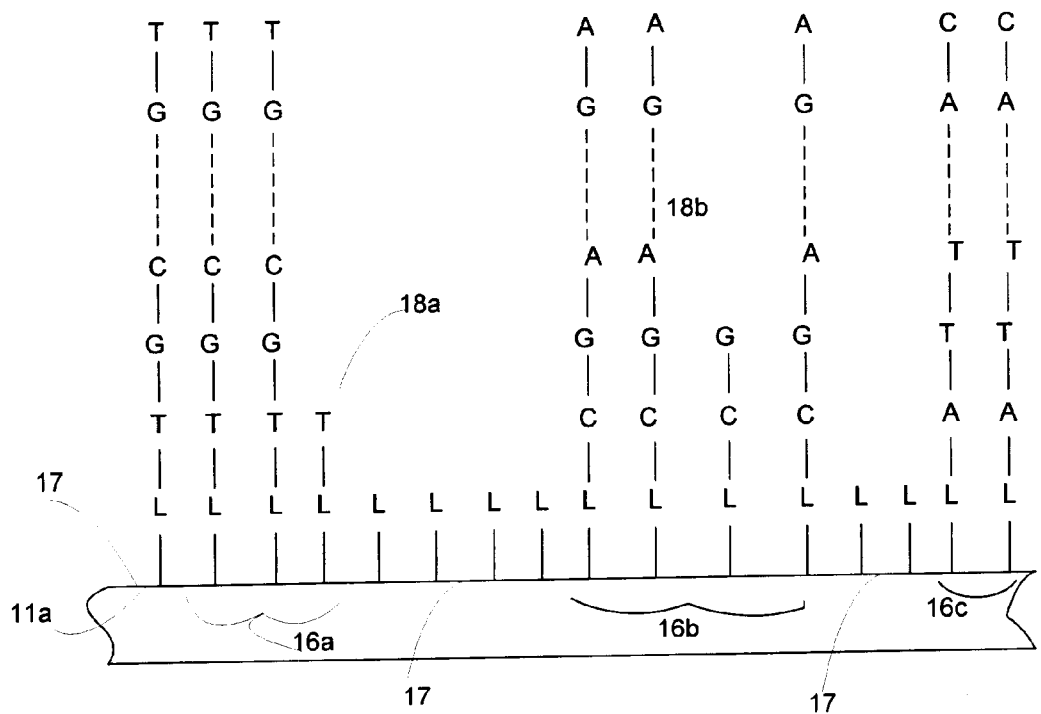
FIG. 5 is an enlarged illustration of a portion of the substrate of FIG. 3.

Referring first to FIGS. 3–5, typically methods and apparatus of the present invention generate or use a contiguous planar substrate 10 carrying one or more arrays 12 disposed across a first surface 11a of substrate 10 and separated by inter-array areas 13. The arrays on substrate 10 can be designed for testing against any type of sample, whether a trial sample, reference sample, a combination of them, or a known mixture of polynucleotides (in which latter case the arrays may be composed of features carrying unknown sequences to be evaluated). While ten arrays 12 are shown in FIG. 5 and the different embodiments described below may use substrates with particular numbers of arrays, it will be understood that substrate 10 and the embodiments to be used with it, may use any number of desired arrays 12. Similarly, substrate 10 may be of any shape, and any apparatus used with it adapted accordingly. Depending upon intended use, any or all of arrays 12 may be the same or different from one another and each will contain multiple spots or features 16 of biopolymers in the form of polynucleotides. A typical array may contain from more than ten, more than one hundred, more than one thousand or ten thousand features, or even more than from one hundred thousand features. All of the features 16 may be different, or some or all could be the same. In the embodiment illustrated, there are interfeature areas 17 between features, which do not carry any polynucleotide. It will be appreciated though, that the interfeature areas 17 could be of various sizes and configurations. Each feature carries a predetermined polynucleotide (which includes the possibility of mixtures of polynucleotides). As per usual, A, C, G, T represent the usual nucleotides, while L represents a linker bound to substrate 10. It will be appreciated that there need not be any space separating arrays 12 from one another, nor features 16 within an array from one another. However, in the preferred case where arrays 12 are formed by the in situ method by depositing droplets of reagents in each step such as by using a pulse jet such as an inkjet type head, such interfeature areas 17 will typically be present.

As already mentioned, the method of the present invention may use a β- or γ-phosphor or phosphite, protected alcohol. β-phosphor or β-phosphite, protected alcohols, have the following structure:

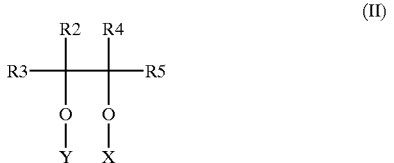

(II)

Wherein: Y—O— is a phosphor or phosphite group as defined above; any of R2, R3, R4 or R5 may be the same or different and may be selected from H, substituted or unsubstituted alkyl or alkoxyl groups (particularly lower alkyl groups), or any two of them may together form a carbocyclic ring or heterocyclic ring (including those having one or two heteroatoms selected from N or O) such as a five to seven membered ring (for example, furyl); and X represents an alcohol protecting group. γ-phosphor or γ-phosphite compounds have the same formula as (II) above, except that there is an additional C (substituted or unsubstituted with one to two groups, the same or different selected from any of those groups which R2 to R5 may represent) between the Cs to which R2 and R4 are bonded. Particularly preferred are those compounds of formula (II) in which two of R2 to R5 form a ring, particularly a 5 membered heterocyclic ring, such as furyl or pyryl (particularly where the compound is a furanose, or pyranose derivative). In cases where a ring is present, it is preferred that Y—O— and X—O— are cis with respect to one another. Suitable protecting groups on the alcohol include those such as described in "Protective groups in organic synthesis" by Theodora W. Greene and Peter G. M. Wuts, Wiley-interscience ISBN 0-471-62301-6 p68–117. The protecting group on the alcohol group substantially prevents one monomer from linking with another through that alcohol group during growing of the polymer chain.

Particular examples of compounds of formulae (II) may include β- or γ-phosphoramidyl, protected alcohols, which are 3-carboxylate-4-phosphoramidylfuran, or 2,5-dialkoxy-3-carboxylate-4-phosphoramidylfuran, or any of those compounds illustrate below:

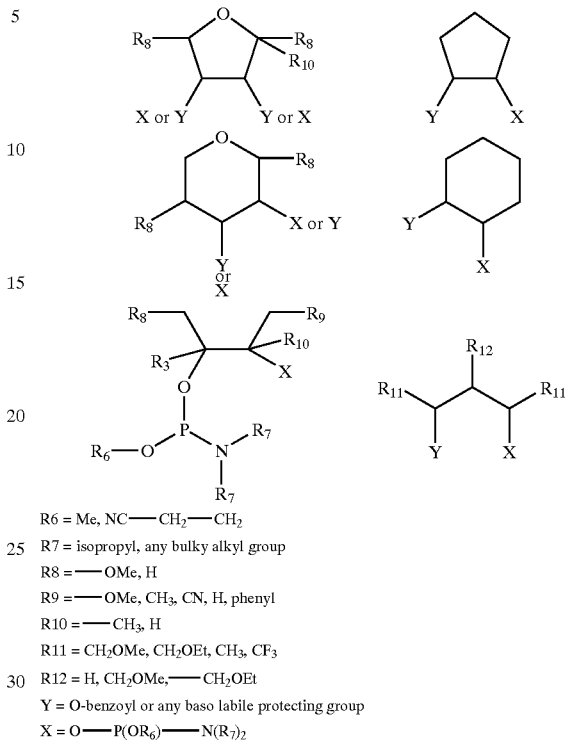

R6 = Me, NC—CH₂—CH₂
R7 = isopropyl, any bulky alkyl group
R8 = —OMe, H
R9 = —OMe, CH₃, CN, H, phenyl
R10 = —CH₃, H
R11 = CH₂OMe, CH₂OEt, CH₃, CF₃
R12 = H, CH₂OMe,—CH₂OEt
Y = O-benzoyl or any baso labile protecting group
X = O—P(OR₆)—N(R₇)₂

Alternatively X may, for example, be an H-phosphonate, Me-phosphonate, or phosphodiester group.

In general the β- or γ- phosphor or phosphite, protected alcohols can be prepared by methods such as described by Toshiki Tanaka and Robert Letsinger, Nucleic Acids Research, 10, 3249–3260, 1982. The β- or γ-phosphoramidyl, protected alcohols, in particular can be prepared by the method described in column 11 and 12 of U.S. Pat. No. 5,681,945 up to product 2, then the remaining alcohol is converted to the cyanoethyl phosphoramidite using 2-cyanoethyl-N, N, N', N'-tetraisopropylphosphorodiamidite (A.Kraszewski, K. E. Norris, Nucleic Acids Res., 18, 177 (1987)). The protected nucleoside (1mmol) and tetrazole (0.5 mmol) are dried under vacuum for 4 hours. These reagents are then dissolved in CH₂Cl₂/THF (95:5, 20 ml), and 2-cyanoethyl-N, N, N', N'-tetraisopropylphosphorodiamidite (1.3 mmol) is added drop-wise under argon. The reaction is stirred 20 hours at room temperature. Triethylamine (0.5 ml) is added to the reaction mixture. The mixture is diluted with CH₂Cl₂ (20 ml) and extracted with 2% aqueous Na₂CO₃ (30 ml) followed by brine (30 ml). The aqueous layers are back extracted with CH₂Cl₂ (30 ml). The combined organic layers are dried over Na₂SO₄. The organic fraction is concentrated to 15 ml and product is precipitated from cold hexane. The precipitate is dried under vacuum.

A typical execution of a method of the present invention is illustrated using a β-phosphor or β-phosphite compound of formula (II). First, normally substrate 10 will have been functionalized by providing it with substrate bound moieties with hydroxy groups. Suitable techniques for functionalizing substrates with such linking moieties are described, for example, in Southern, E. M., Maskos, U. and Elder, J. K., Genomics, 13, 1007–1017, 1992. In the manufacture of an array as illustrate in FIGS. 3–5 this step is normally carried out by exposing the substrate 10 (in particular, first surface 11a of substrate 10) to functionalizing reagents as described in the foregoing references. Next, a nucleoside phosphor or phosphite compound is then deposited as a droplet of solution onto each address on substrate 10 at which it is desired to form a features 16, using any suitable droplet deposition technique as discussed above, such as a pulse jet (for example, and inkjet head). Such a nucleoside compound typically has the phosphor or phosphite group at one of the 3' or 5' positions, depending upon which direction (3' to 5', or 5' to 3') it is desired to have the polynucleotide synthesis proceed, and a protected hydroxy group at the other one of those positions. Nucleoside phosphoramidites are preferred. Suitable protecting groups are described in "Protective Groups in Organic Synthesis" by T. W. Green, Wiley Interscience. The protecting group should be capable of removal to deprotect the hydroxy group, under first deprotection conditions. The first deprotection conditions preferably are acidic conditions, and thus acid labile protecting groups are preferred. Acid labile protecting groups include those such as tetrahydropyranyl groups, e.g. tetrahydropyran-2-yl and 4-methoxytetrahydropyran-2-yl; optionally substituted trityl groups, for example a monomethoxytrityl for oligoribonucleotide synthesis and a dimethoxytrityl for oligodeoxyribonucleotide synthesis, pixyl; isobutyloxycarbonyl; t-butyl; and dimethylsilyl. The preferred acid labile protecting group is a dimethoxytrityl group, especially 4,4'-dimethoxytrityl. Conventional known reaction conditions may be used. As a result, the nucleoside compound is coupled to the hydroxy groups of at least some of the substrate bound linking groups, by forming the corresponding phosphor or phosphite between the hydroxy groups of the substrate bound linkers and the phosphor or phosphite group (for example, phosphoramidyl group) of the nucleoside compound. Particularly in the case of phosphoramidites, the reaction is complete very rapidly at room temperature of about 20° C. (for example, in one or two seconds).

The coupling product is then oxidized using known conditions (described in one or more of the references cited above) to form the more stable corresponding phosphate bond between the nucleoside and linker. This is preferably performed by exposing substrate 10 (in particular, the entire first surface 11a) to the oxidizing solution, for example, by flowing such a solution across first surface 11a. Note that this oxidation step is optional, although preferred.

At this point, the capping of substrate bound linkers which failed to couple with a nucleoside compound, can then be accomplished by exposing substrate 10 (in particular, the entire first surface 11a) to such reagent. This also is preferably accomplished by flowing a solution containing any of the capping reagents of formula (II) described above across first surface 11a. Suitable solvents and reactions conditions include any of those which may be used to couple analogous nucleoside phosphor or phosphite compounds to the linker, as described above. By analogous in this context, is referenced the same phosphor or phosphite group being present. Note that the alcohol protecting group, X, should be one which is removed under second deprotection conditions but not removed under the first deprotection conditions. By "not removed under the first deprotection conditions" is referenced one of which no more than 40%, 20%, or 10% is removed (and preferably no more than 5%, and most preferably no more than 2%). The second deprotection conditions are preferably alkaline, and thus X is preferably an alkaline labile deprotecting group. Suitable alkaline deprotecting groups are also described in "Protective Groups in Organic Synthesis", supra. Examples of protecting groups X include benzoyl, acetyl, p-nitrophenyl carbonate groups, silyl protecting groups (for example, as dimethyl silyl) which can be removed with a fluoride anion such as tetrabutylammonium fluoride. Particularly preferable are ones which provide, on the protected alcohol, a carboxylate group such as an alkyl carboxylate group (particularly a lower carboxylate group), such as acetate.

Following the coupling, oxidation, and capping steps as described above, substrate 10 (particularly first surface 11a) may then be exposed to the first deprotection conditions (preferably by exposure to an acidic solution as already described), to deprotect the protected 3' or 5' hydroxy of the coupled nucleoside. The required solution is, for example, flowed across first surface 11a. The steps of coupling, oxidation, capping, and deprotection of the coupled nucleoside may then be repeated until each feature 16 has the desired polynucleotide sequence. Note that in each repetition of the cycle of steps, the deprotected hydroxy group of a coupled nucleoside in a given cycle, serves as the hydroxy group of substrate bound moieties in the next cycle.

Figure 6:
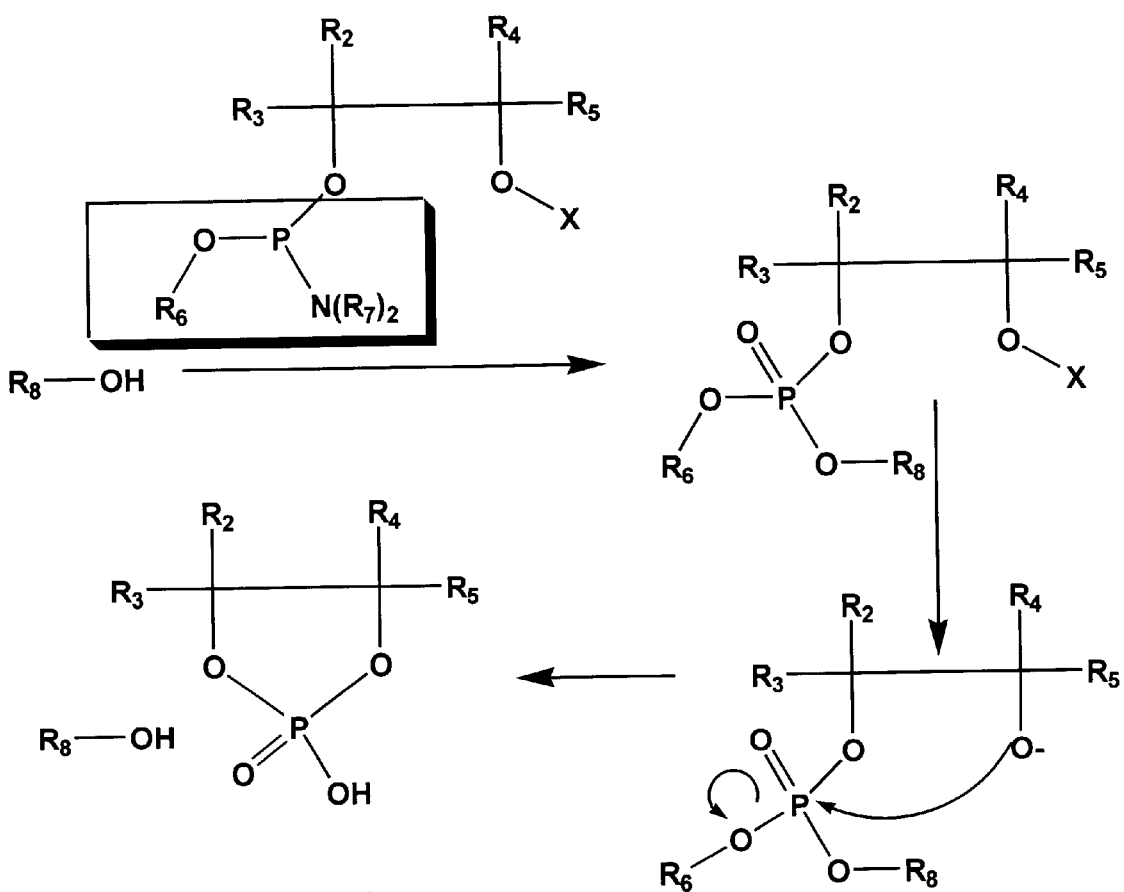
FIG. 6 is a schematic illustrating in general a capping and de-capping method of the present invention.

At this point, the substrate 10 (particularly first surface 11a) is exposed to the second deprotection conditions. This also may be done by flowing the required alkaline solution across the entire first surface 11a. As a result, failed sequences resulting from each cycle of the steps, will be deprotected, as illustrated in FIG. 6, by hydrolysis to deprotect the protected alcohol of such sequences and cleave the phosphate from the substrate bound moiety (whether a nucleotide or linker) so as to regenerate the hydroxy group of the substrate bound moiety.

Figure 7:
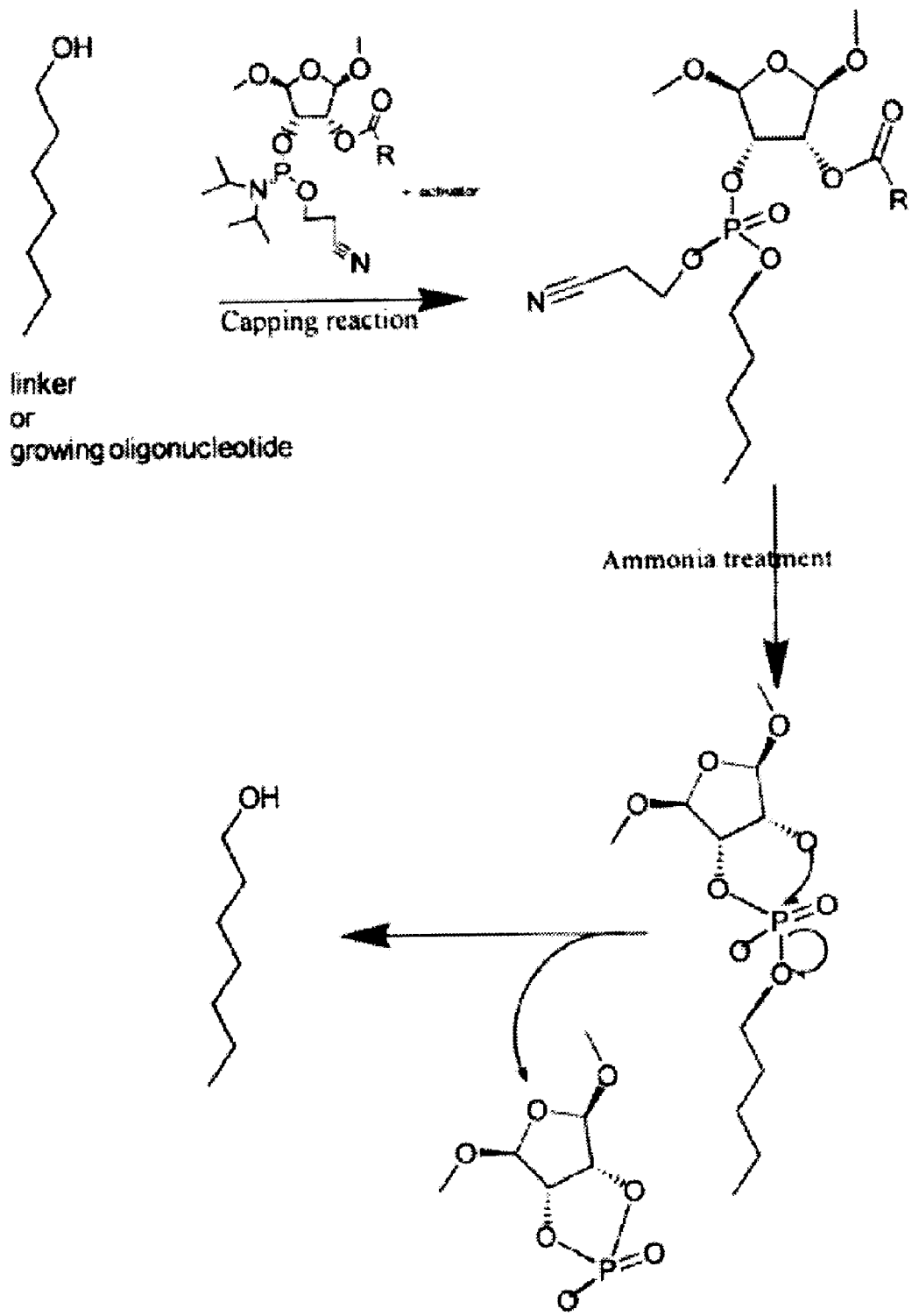
FIG. 7 is a schematic illustrating a specific capping and de-capping method of the present invention.

A particular example of the method of the present invention is illustrate in FIG. 7 (in which "R" is any one of the lower alkyls, particularly methyl). The illustrate steps may be executed as follows. During the capping step, an equal amount of a solution of a capping phosphoramidite and an activator (such as tetrazole) are flooded over the surface. The solutions are either premixed or mixed on the surface. After 1 minute the solution is removed from the surface and an oxidation solution is flooded over the surface. At the end of the synthesis, the DNA array is removed from the synthesizer and is dipped in 600 ml of a 1:1 solution of a 40% methylamine in water and 28% ammonia in water. This solution removes the protecting groups on the DNA and the capping agent. Then the alcoholate generated on the capping agent attacks the phosphorus leading to a cleavage of the P-O bond. After 16 hours at room temperature the arrays are removed from the solution and washed with water. The DNA array is ready to be use. In the case where other capping agents are used in accordance with the methods of the present invention, the foregoing conditions can be adjusted accordingly.

Various modifications to the particular embodiments described above are, of course, possible. Accordingly, the present invention is not limited to the particular embodiments described in detail above.

What is claimed is:

1. A method of capping and de-capping a hydroxy group of a moiety, comprising:
   (a) coupling the hydroxy group of the moiety to a β- or γ-phosphoramidyl, protected alcohol, so as to form the corresponding phosphite between the hydroxy and phosphoramidyl groups;
   (b) oxidizing the phosphite to a phosphate; and
   (c) de-capping the hydroxy group by hydrolyzing the resulting compound to deprotect the protected alcohol and cleave the phosphate from the moiety so as to regenerate the hydroxy group of the moiety.

2. A method according to claim 1 wherein a β-phosphoramidyl, protected alcohol is coupled to the hydroxy group of the moiety.

3. A method according to claim 1 wherein the hydrolysis is performed under alkaline conditions.

4. A method of synthesizing oligonucleotides on a substrate carrying substrate bound moieties each with a hydroxy group, comprising:
   (a) coupling a nucleoside phosphoramidite to the hydroxy group of at least some of the substrate bound moieties by forming the corresponding phosphite between the hydroxy groups of the substrate bound moieties and the phosphoramidyl groups of the nucleoside phosphoramidite, wherein the nucleoside has a protected hydroxy which can be deprotected under first deprotection conditions; and
   (b) capping at least some of the substrate bound moieties which failed to couple with the nucleoside phosphoramidite by exposing them to a β- or γ-phosphoramidyl, protected alcohol so as to form the corresponding phosphite between the hydroxy of those substrate bound moieties and phosphoramidyl group of the β- or γ-phosphoramidyl, protected alcohol, wherein the protected alcohol can be deprotected under second deprotection conditions but not under the first deprotection conditions.

5. A method according to claim 4 further comprising:
   (c) oxidizing phosphites formed in steps (a) and (b) to phosphates.

6. A method according to claim 4 further comprising:
   (d) following steps (a) and (b), exposing the substrate to the first deprotection conditions to deprotect the protected hydroxy of the coupled nucleoside;
   (e) repeating steps (a) to (d) wherein the deprotected hydroxy of the coupled nucleoside from step (d) in one cycle of the steps, serves as the hydroxy group of substrate bound moieties in the next cycle; and
   (f) following step (e), exposing the substrate to the second deprotection conditions to de-cap failed sequences by hydrolysis to deprotect the protected alcohol and cleave the phosphate from the substrate bound moiety so as to regenerate the hydroxy group of the substrate bound moiety.

7. A method according to claim 6 wherein the second deprotection conditions are alkaline conditions.

8. A method according to claim 6 wherein the first deprotection conditions are acidic conditions.

9. A method according to claim 7 wherein the at least some of the substrate bound moieties which failed to couple are exposed to a β-phosphoramidyl, protected alcohol.

10. A method of synthesizing oligonucleotides on a substrate carrying substrate bound moieties each with a hydroxy group, comprising:
    (a) coupling a nucleoside phosphoramidite to the hydroxy group of at least some of the substrate bound moieties, which first nucleoside has a protected hydroxy which can be deprotected under first deprotection conditions, by forming the corresponding phosphite between the hydroxy groups of the substrate bound moieties and the phosphoramidyl groups of the first nucleoside phosphoramidite, wherein the nucleoside has a protected hydroxy which can be deprotected under first deprotection conditions;
    (b) capping at least some of the substrate bound moieties which failed to couple with the nucleoside phosphoramidite by exposing them to a β- or γ-phosphoramidyl, protected alcohol, which protected alcohol can be deprotected under second deprotection conditions but not the first deprotection conditions, so as to form the corresponding phosphite between the hydroxy of those substrate bound moieties, and phosphoramidyl group of the β- or γ-phosphoramidyl, protected alcohol, wherein the protected alcohol can be deprotected under second deprotection conditions but not under the first deprotection conditions;
    (c) oxidizing phosphites formed in steps (a) and (b) to phosphates;
    (d) following steps (a) and (b), exposing the substrate to the first deprotection conditions to deprotect the protected hydroxy of the coupled nucleoside;
    (e) repeating steps (a) to (d) wherein the deprotected hydroxy of the coupled nucleoside from step (d) in one cycle of the steps, serves as the hydroxy group of substrate bound moieties in the next cycle; and
    (f) following step (e), exposing the substrate to the second deprotection conditions to de-cap failed sequences by hydrolysis to deprotect the protected alcohol and cleave the phosphate from the substrate bound moiety so as to regenerate the hydroxy group of the substrate bound moiety;
    wherein the protected alcohol of the β- or γ-phosphoramidyl, protected alcohol, has a carboxylate group.

11. A method according to claim 10 wherein the β- or γ-phosphoramidyl, protected alcohol, is a carbocyclic or heterocyclic compound.

12. A method according to claim 11 wherein the phosphoramidyl and protected alcohol are cis.

13. A method according to claim 11 wherein the β- or γ-phosphoramidyl, protected alcohol, is a furanose or pyranose derivative.

14. A method according to claim 13 wherein the β- or γ-phosphoramidyl, protected alcohol, is a 3-carboxylate-4-phosphoramidylfuran.

15. A method according to claim 14 wherein the β- or γ-phosphoramidyl, protected alcohol, is a 2,5-dialkoxy-3-carboxylate-4-phosphoramidylfuran.

16. A method of fabricating an addressable array of polynucleotides on a substrate carrying substrate bound moieties each with a hydroxy group, comprising, at each of multiple different substrate addresses:
    (a) coupling a nucleoside phosphoramidite to the hydroxy group of at least some of the substrate bound moieties by forming the corresponding phosphite between the hydroxy groups of the substrate bound moieties and the phosphoramidyl groups of the first phosphoramidite, wherein the nucleoside has a protected hydroxy which can be deprotected under first deprotection conditions; and
    (b) capping at least some of the substrate bound moieties which failed to couple with the nucleoside phosphoramidite by exposing them to a β- or γ-phosphoramidyl, protected alcohol so as to form the corresponding phosphite between the hydroxy of those substrate bound moieties, and phosphoramidyl group of the β- or γ-phosphoramidyl, protected alcohol, wherein the protected alcohol can be deprotected under second deprotection conditions but not the first deprotection conditions;
    (c) oxidizing phosphites formed in steps (a) and (b) to phosphates;
    (d) following steps (a) and (b), exposing the addresses to the first deprotection conditions to deprotect the protected hydroxy of the coupled nucleoside;

(e) repeating steps (a) to (d) wherein the deprotected hydroxy of the coupled nucleoside from step (d) in one cycle of the steps, serves as the hydroxy group of substrate bound moieties in the next cycle, so as to form different polynucleotide sequences at different addresses; and (f) following step (e), exposing the substrate to the second deprotection conditions to de-cap failed sequences by hydrolysis to deprotect the protected alcohol and cleave the phosphate from the substrate bound moiety so as to regenerate the hydroxy group of the substrate bound moiety.

17. A method according to claim 16 wherein in step (a) the phosphoramidites to be coupled at respective addresses are deposited as droplets at those addresses, and wherein in step (b) both the addresses and inter-address areas are exposed to the β- or γ-phosphoramidyl, protected alcohol.

18. A method according to claim 16 wherein in step (b) all of the substrate is simultaneously exposed to the β- or γ-phosphoramidyl, protected alcohol.

19. If A method according to claim 18 wherein in step (f) all of the substrate is simultaneously exposed to the β- or γ-phosphoramidyl, protected alcohol.

20. A method according to claim 16 wherein the second deprotection conditions are alkaline conditions.

21. A method according to claim 16 wherein the at least some of the substrate bound moieties which failed to couple are exposed to a phosphoramidyl, protected alcohol.

22. A method of fabricating an addressable array of polynucleotides on a substrate carrying substrate bound moieties each with a hydroxy group, comprising, at each of multiple different substrate addresses:

(a) coupling a nucleoside phosphoramidite to the hydroxy group of at least some of the substrate bound moieties by forming the corresponding phosphite between the hydroxy groups of the substrate bound moieties and the phosphoramidyl groups of the first phosphoramidite, wherein the nucleoside has a protected hydroxy which can be deprotected under first deprotection conditions; and (b) capping at least some of the substrate bound moieties which failed to couple with the nucleoside phosphoramidite by exposing them to a β- or γ-phosphoramidyl, protected alcohol so as to form the corresponding phosphite between the hydroxy of those substrate bound moieties, and phosphoramidyl group of the β- or γ-phosphoramidyl, protected alcohol, wherein the protected alcohol can be deprotected under second deprotection conditions but not the first deprotection conditions;

(c) oxidizing phosphites formed in steps (a) and (b) to phosphates;

(d) following steps (a) and (b), exposing the addresses to the first deprotection conditions to deprotect the protected hydroxy of the coupled nucleoside;

(e) repeating steps (a) to (d) wherein the deprotected hydroxy of the coupled nucleoside from step (d) in one cycle of the steps, serves as the hydroxy group of substrate bound moieties in the next cycle, so as to form different polynucleotide sequences at different addresses; and (f) following step (e), exposing the substrate to the second deprotection conditions to de-cap failed sequences by hydrolysis to deprotect the protected alcohol and cleave the phosphate from the substrate bound moiety so as to regenerate the hydroxy group of the substrate bound moiety;

wherein the nucleoside has a carboxylate group.

23. A method according to claim 22 wherein the β- or γ-phosphoramidyl, protected alcohol, is a furanose or pyranose derivative.

24. A method according to claim 22 wherein the β- or γ-phosphoramidyl, protected alcohol, is a 2,5-dialkoxy-3-carboxylate-4-phosphoramidylfuran.

* * * * *